(12) United States Patent
Beckmann et al.

(10) Patent No.: US 10,303,355 B2
(45) Date of Patent: May 28, 2019

(54) METHOD, GRAPHICAL INTERFACE, AND MEDICAL APPARATUS FOR PLANNING A MEDICAL IMAGING EXAMINATION

(71) Applicant: Siemens Aktiengesellschaft, Munich (DE)

(72) Inventors: Marc Beckmann, Bubenreuth (DE); Anja Jaeger, Fuerth (DE); Stephan Nufer, Erlangen (DE); Thorsten Speckner, Erlangen (DE); Jens Thoene, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 301 days.

(21) Appl. No.: 15/067,759

(22) Filed: Mar. 11, 2016

(65) Prior Publication Data

US 2016/0266760 A1 Sep. 15, 2016

(30) Foreign Application Priority Data

Mar. 13, 2015 (DE) ........................ 10 2015 204 628

(51) Int. Cl.
| | |
|---|---|
| *G06F 3/01* | (2006.01) |
| *G06F 3/0484* | (2013.01) |
| *A61B 5/00* | (2006.01) |
| *A61B 34/10* | (2016.01) |
| *G06F 3/0488* | (2013.01) |
| *A61B 5/055* | (2006.01) |

(52) U.S. Cl.
CPC .......... *G06F 3/0488* (2013.01); *A61B 5/0033* (2013.01); *A61B 5/055* (2013.01); *A61B 5/7475* (2013.01); *A61B 34/10* (2016.02); *G06F 3/016* (2013.01); *G06F 3/04847* (2013.01); *G06F 2203/04809* (2013.01)

(58) Field of Classification Search
CPC .................................................. G01R 33/3415
USPC ................................ 715/700, 740, 743, 715
See application file for complete search history.

(56) References Cited

U.S. PATENT DOCUMENTS

| | | | |
|---|---|---|---|
| 7,433,503 B2 | 10/2008 | Cherek et al. | |
| 8,390,290 B2* | 3/2013 | Sukkau | G01R 33/3415 |
| | | | 324/318 |
| 8,920,368 B2* | 12/2014 | Sandhu | A61B 34/25 |
| | | | 604/95.01 |
| 9,753,111 B2 | 9/2017 | Forthmann et al. | |
| 2002/0118280 A1 | 8/2002 | Medlar et al. | |
| 2004/0122311 A1* | 6/2004 | Cosman | A61B 6/5247 |
| | | | 600/427 |

(Continued)

FOREIGN PATENT DOCUMENTS

| | | |
|---|---|---|
| CN | 101209368 A | 7/2008 |
| DE | 102011077892 A1 | 12/2012 |

*Primary Examiner* — Cao H Nguyen
(74) *Attorney, Agent, or Firm* — Schiff Hardin LLP

(57) ABSTRACT

In a method for planning a medical imaging examination, as well as a graphical interface and a medical imaging apparatus and a storage medium for implementing the method, a planning environment for the planning of the medical imaging examination is provided on a touch display of a graphical interface, at least one imaging parameter for the medical imaging examination is specified by a manual input on the touch display, and information is provided on the touch display in response to the manual input, the information being presented haptically on the touch display.

20 Claims, 3 Drawing Sheets

(56) References Cited

U.S. PATENT DOCUMENTS

| | | |
|---|---|---|
| 2010/0156421 A1 | 6/2010 | Sukkau |
| 2012/0268285 A1 | 10/2012 | Hansen |
| 2013/0165854 A1 | 6/2013 | Sandhu et al. |
| 2016/0202864 A1* | 7/2016 | Hardie ................ G01R 33/307 715/771 |
| 2016/0367169 A1 | 12/2016 | Hardie et al. |

* cited by examiner

METHOD, GRAPHICAL INTERFACE, AND MEDICAL APPARATUS FOR PLANNING A MEDICAL IMAGING EXAMINATION

BACKGROUND OF THE INVENTION

Field of the Invention

The invention concerns a method for planning a medical imaging examination, as well as to a graphical interface unit, a medical imaging apparatus and a non-transitory, computer-readable data storage medium for implementing such a method.

Description of the Prior Art

In a medical imaging examination, medical image data of an examination subject are acquired by the operation of a medical imaging apparatus. The medical image data can represent anatomical structures and/or functional processes of the body of the examination subject. The medical imaging examination typically requires a planning process. Normally, during the planning process, at least one imaging parameter must be specified for the medical imaging examination. The planning is usually carried out at least in part by a user who specifies the at least one imaging parameter.

SUMMARY OF THE INVENTION

An object of the invention is to improve such planning of a medical imaging examination.

The inventive method for planning a medical imaging examination of an examination subject by operation of a medical imaging apparatus includes the following steps.

A planning environment for the planning of the medical imaging examination is provided on a touch display of a graphical interface.

At least one imaging parameter for the medical imaging examination is specified by a manual input on the touch display.

Information is provided on the touch display dependent on the manual input, the information being presented haptically on the touch display.

The examination subject can be a patient, a volunteer for training the system, an animal or a phantom.

The graphical interface unit is in particular a visualization unit and/or an output unit for the presentation and/or graphical output of information to a user, in particular a member of the medical operating staff (operator). Furthermore, the graphical interface unit can also be configured for the input of information, in particular for the specification of the at least one medical imaging parameter, by a medical operator.

The graphical interface preferably is a graphical output unit, more specifically the touch display. Such a touch display makes it particularly simple to visualize information and to enter the at least one medical imaging parameter as an input. The touch display can in this case be directly arranged on the medical imaging apparatus so that there is no need for a medical operator to leave the examination room in which the medical imaging apparatus is situated for that purpose. In this situation the graphical interface unit is preferably arranged on a housing that encloses the scanner of the medical imaging apparatus.

A touch display, also known as a touchscreen, is a touch-sensitive screen. When portions of the screen, in particular portions of an image displayed on the screen, are touched, parameters, for example the at least one medical imaging parameter, can be entered. The touch display accordingly represents a combined input and output device. One of the user's fingers and/or a stylus are/is preferably used for entering the parameter via the touch display. The input in this case can be accomplished by approaching the touch display with the finger and/or the stylus. Alternatively, an input can occur after the touching of the display satisfied a condition, for example when a certain pressure point is exceeded or a capacitance value is reached.

The planning environment that is provided on the touch display can facilitate the planning of the medical imaging examination. The at least one imaging parameter for the medical imaging examination can be specified on the planning environment. On completion of the planning, the medical imaging can be performed using the specified at least one imaging parameter. The planning environment can include a graphical visualization of the examination subject, as described in greater detail below. This enables the at least one imaging parameter to be specified directly on the graphical representation of the examination subject. The graphical representation of the examination subject may have been acquired in advance by a camera, in particular if the examination subject is still positioned outside of a patient receiving zone of the medical imaging device. Alternatively or in addition, the planning environment can include image data of an overview measurement (localizer, scout), in which case the further workflow sequence of the medical examination is planned on the basis of the image data of the overview measurement.

For the purpose of planning the medical imaging examination, the examination subject is already positioned on a patient support apparatus of the medical imaging device. In addition, all preparatory activities for the upcoming medical imaging examination on the examination subject will already have been completed. In this case all the accessory units required for the upcoming medical imaging examination, such as local radio-frequency antenna units for the magnetic resonance imaging, for example, are already positioned on the examination subject. Furthermore, the patient support apparatus, in particular a patient support and positioning table of the patient support apparatus, is still situated outside of the patient receiving zone of the medical imaging scanner at the beginning of the planning of the medical imaging examination. The patient support apparatus is already disposed in a position in relation to the patient receiving zone that is ready to allow the examination subject to be introduced into the patient receiving zone. Alternatively, the examination subject can already be positioned in the patient receiving zone for the planning of the medical imaging examination.

The at least one imaging parameter can specify a setting on the basis of which the following examination of the examination subject by the medical imaging device is controlled. The at least one imaging parameter can include, for example, a positioning and/or geometry and/or a size of a field of view for the medical imaging examination. The field of view for an overview measurement (localizer), in particular an extent of the field of view in an axial direction along a longitudinal axis of the examination subject, can also be specified. For example, the at least one imaging parameter can be a position of imaging slices. The at least one imaging parameter can be a selection of an imaging mode, as well as a selection of parameters, in particular characteristics, of the examination subject. The at least one imaging parameter can also include a specification of a position of an isocenter, in particular directly on the graphical visualization of the examination subject on the touch display.

The specification of the at least one imaging parameter is effected by a manual input, for example a manual gesture, by the user on the graphical interface unit, in particular on the touch display. In this way the at least one imaging parameter can be specified particularly quickly by a gesture on the part of an operator. As a result, it is possible to dispense with a time-consuming and cumbersome specification based on an input with the use of an additional input device, such as a keyboard with cursor keys. The manual gesture preferably is a sliding and/or swiping and/or dragging of at least one of the user's fingers over the graphical interface unit, in particular over the touch display. A manual gesture in this context is a gesture that the medical operator makes directly at and/or on the graphical interface, in particular the touch display. An input command, a choice of the at least one imaging parameter for example, is uniquely assigned to the manual gesture.

The information is provided as a function of the specification of the at least one imaging parameter on the touch display. In this way, as described below, the information can serve as feedback in response to the specification of the at least one imaging parameter. It is also conceivable for the information to be provided on the touch display already prior to the specification of the at least one imaging parameter, so that the specification of the at least one imaging parameter can be carried out taking into account and/or with the assistance of the provided information. The information on the touch display is provided to the user who specifies the at least one imaging parameter by the manual input on the touch display. In this way the information provided on the touch display can represent an immediate assistance and/or instant feedback regarding the specification of the at least one imaging parameter.

According to the invention, the user is provided with information that is presented haptically on the touch display. This means that the user haptically perceives the information on the touch display, in particular with his or her fingers, by which he or she actuates the manual input on the touch display in order to specify the at least one imaging parameter. The information can thus be sensed by the user with his or her fingers. The information can be presented, for example, in such a way that it represents a haptically perceivable stimulus, such as in the form of pressure and/or vibration and/or pain and/or temperature and/or distension. The information can then be perceived by the user by mechanoreceptors in the skin of the finger and/or by vibration receptors in tendons, joints or muscles. Haptically presenting the information on the touch display can include presenting the information as a tactile change to a surface structure of the touch display. Haptically presenting the information on the touch display is intended to exclude a merely audible and/or visual presentation of the information. The fact that the information is presented haptically is also intended to include the possibility of a tactile presentation of the information on the touch display. The information is provided directly on the touch display.

Haptically providing the information during the planning of the medical imaging examination affords a particularly advantageous opportunity for improving and/or simplifying the planning of the medical examination. The haptically presented information allows the user to be alerted particularly quickly and/or clearly as to errors during the planning of the medical imaging examination, or to an invalid and/or inconsistent specification of the at least one imaging parameter, for example. The user can accordingly respond particularly rapidly to unreliable or at least unfavorable user inputs. In this way the user's attention can be drawn particularly quickly to a specific, possibly problematic, situation during the planning of the medical imaging examination. Because of the haptically presented information, the user can furthermore also be provided with valuable supplementary information for the planning of the medical imaging examination. Thus, for example, a contour of the examination subject can be provided in tactile form as information on the touch display for the user. In this way a more accurate positioning of the field of view for the medical imaging examination can be carried out by the user. In particular, haptically providing the information on the touch display advantageously enables the user's attention to be heightened. The haptically presented information can facilitate a multimodal interaction of the user with the touch display. In this way it is possible to reduce the number of errors made by the user during the planning of the medical imaging examination. A degree of assurance of the user during the planning of the medical imaging examination can thus be increased and/or a learning effect achieved.

It is advantageous for the user to be provided with further information by way of a different sensory modality in addition to the haptically presented information. Thus, for example, the user can be provided with visual or audible information in addition to the haptically presented information. In this way it is possible to provide the user with signals and/or information relating to the planning of the medical imaging examination on different channels, through haptic and optical perception, for example.

An embodiment variant provides that the information on the touch display is provided as an acknowledgment of the specification of the at least one imaging parameter. In this way the user can receive an immediate acknowledgment, also known as feedback, in response to the specification of the at least one imaging parameter. The feedback is presented haptically. The feedback can be provided as a function of the specification of the at least one imaging parameter, for example as a function of a specified value of the at least one imaging parameter. The feedback can be provided as a function of a validity check on a value specified by the user for the at least one imaging parameter. In particular the feedback is provided, advantageously instantly, after the specification of the at least one imaging parameter in time. The feedback can accordingly provide information concerning the validity and/or reliability of the specified imaging parameter. For example, it can be signaled directly to the user whether he or she has possibly selected an invalid or at least unfavorable value for the at least one imaging parameter. The feedback can direct the user's attention to invalid or at least unfavorable inputs of the at least one imaging parameter. In this way a new input and/or a change to the at least one imaging parameter can be initiated immediately by the user. The user can particularly advantageously be alerted to errors during the specification of the at least one imaging parameter.

In an embodiment, the at least one specified imaging parameter is compared with a parameter range for the at least one imaging parameter and the feedback is provided on the touch display as a function of a result of the comparison. The parameter range for the at least one imaging parameter can be, as described below, be a valid range for the at least one imaging parameter. In particular, the planning of the medical imaging examination can require a specification of the at least one imaging parameter within the, in particular valid, parameter range. It is also conceivable that the medical imaging of the examination subject will generate qualitatively inferior results if the at least one imaging parameter is selected outside of the, in particular valid, parameter range. The valid parameter range can accordingly also represent a particularly favorable value range for the at least one imaging parameter. Alternatively, it is conceivable that the parameter range represents an invalid and/or prohibited range for the at least one imaging parameter. The valid parameter range can be specified manually or automatically in advance, in particular on the basis of known characteristics of the medical imaging device. The valid parameter range can also be chosen as a function of a completed preparation of the examination subject for the medical imaging examination. Overall, the proposed approach enables a particularly simple validity check for the choice of the at least one imaging parameter.

In another embodiment, the parameter range represents a valid parameter range for the at least one imaging parameter, the feedback being provided on the touch display when the result of the comparison of the at least one specified imaging parameter with the parameter range is that the at least one specified imaging parameter lies outside of the valid parameter range for the at least one imaging parameter. Such a check can for example be performed continuously such that a possible change to the at least one imaging parameter is in turn compared with the valid parameter range. Values of the at least one imaging parameter that are beneficial and/or valid and/or suitable for the imaging can be present within the valid parameter range. The fact that the parameter range is referred to as a valid parameter range can also include that a medical imaging session is still possible with a setting of the at least one imaging parameter outside of the valid parameter range, although qualitatively inferior imaging results are likely in that case. It is alternatively also conceivable that a setting of the at least one imaging parameter outside of the valid parameter range makes a medical imaging session impossible. In particular, the valid parameter range has an upper limit and/or a lower limit for a value of the at least one imaging parameter. The at least one specified imaging parameter is located outside of the valid parameter range in particular when the value of the at least one imaging parameter is specified such that it is greater than the upper limit and/or less than the lower limit.

In another embodiment, the feedback is provided continuously until a specification of the at least one imaging parameter falls within the valid parameter range. In this way the user can be alerted in particular continuously to an unfavorable and/or invalid input of the at least one imaging parameter. The feedback can continue in particular as long as the unfavorable choice of the at least one imaging parameter persists. The user can in this way be urgently requested to change the at least one imaging parameter so that it has a value that falls within the valid parameter range. This approach is beneficial when the invalid choice of the at least one imaging parameter would lead to serious errors in the medical imaging and/or to a non-functioning of the medical imaging.

In another embodiment, the feedback is provided only once, as soon as the at least one imaging parameter is set such that it lies outside of the valid parameter range. In this way the user can be alerted once only to an unfavorable and/or invalid input of the at least one imaging parameter. This approach is beneficial in particular when the specification of the at least one imaging parameter outside of the valid parameter range has caused a change to an imaging mode for the medical imaging. In this way the user can be alerted only once to the change to the imaging mode. The user can be provided with a transition point between the two imaging modes in a tactile form.

In another embodiment, the at least one imaging parameter is a position of the examination subject in relation to an isocenter of the medical imaging scanner. Ideal conditions for a medical imaging examination are to be found in an isocenter of the medical imaging scanner. For example, the isocenter of a magnetic resonance scanner is situated in a region having a maximally homogeneous magnetic field. For the purposes of a magnetic resonance examination, the examination subject, in particular a region of the examination subject that is to be examined, should be arranged as precisely as possible in this homogeneity region or in the isocenter. An isocenter in this context is a point and/or a region that is located within a patient receiving zone and in which, within the medical imaging device, the best conditions for the medical imaging examination are to be found during an operation of the medical imaging device. Preferably the isocenter describes a point inside an isocenter region. The isocenter for the medical imaging device is preferably specified only once at the time of the installation of the medical imaging device. In order to specify the position of the examination subject in relation to the isocenter, at least one localization point is determined by the graphical interface unit, in particular in a graphical visualization of the examination subject on the touch display. A localization point means a point on the graphical visualization of the examination subject that specifies a position and/or a region on the examination subject, the specified position and/or the specified region on the examination subject closely coinciding with an examination position of the examination subject within the patient receiving zone preferably coinciding completely with the isocenter. By this inventive embodiment, an easy and quick specification of a position of the examination subject in relation to an isocenter of a medical imaging apparatus is made possible. A direct feedback on the positioning of the examination subject in relation to the isocenter can also be provided for the user.

In another embodiment, the valid parameter range for the position of the examination subject in relation to the isocenter is a region of the examination subject's body that has been prepared for the medical imaging examination. The region of the body that has been prepared for the medical imaging examination represents that region of the examination subject's body of which medical image data is to be acquired in the medical imaging examination. The valid parameter range is in particular limited to said region of the examination subject's body. In this way a feedback, for example a vibration, is provided if the position of the examination subject has been specified such that the region of the body is situated outside of the isocenter and/or at a distance from the isocenter. In this way the user can be alerted to change the position of the examination subject in relation to the isocenter in a suitable manner. A continuous haptically presented feedback, as described above, is beneficial in this case. In the event of an unfavorable positioning of the examination subject in relation to the isocenter, the user can furthermore be provided in addition with an optical feedback, for example by highlighting of a shape and/or color in the graphical visualization. By this approach, the user can particularly advantageously be alerted to an unfavorable positioning of the examination subject in relation to the isocenter. The unfavorable positioning can accordingly be averted and a non-functioning of the medical imaging examination and/or an inferior quality of the acquired medical image data is thereby prevented.

In another embodiment, the position of at least one accessory unit for the medical imaging examination is detected, the region of the examination subject's body that has been prepared for the medical imaging examination being determined on the basis of the detected position of the at least one accessory unit. The at least one accessory unit can in particular support and/or facilitate imaging of the examination subject by the medical imaging apparatus. The at least one accessory unit can be fixed to a patient support apparatus, for example. Free positioning of the at least one accessory unit on the examination subject is also conceivable. If the medical imaging examination is a magnetic resonance examination, the at least one accessory unit can be a local radio-frequency antenna unit. The at least one accessory unit then has a coil positioned on the examination subject. For example, the accessory unit can also be a local knee radio-frequency antenna unit for a knee examination or a local head radio-frequency antenna unit for a head examination. The position of the at least one accessory unit can be detected with the use of optical signals from the accessory unit that have been acquired by a camera, for example. The position of the at least one accessory unit can then be identified by means of pattern recognition. Alternatively or in addition, the at least one accessory unit can be provided with invisible or visible, marking elements in order to ensure a reliable detection of the at least one accessory unit. Furthermore, the marking elements can be dependent on a type of the at least one accessory unit, such that in addition it will be possible to distinguish between multiple accessory units and/or to classify the at least one accessory unit on the basis of the acquired positional data and/or on the basis of acquired marking data. By the described approach, a position of the examination subject in relation to the isocenter can be specified and/or checked on the basis of a position of the accessory unit. In this way it can be ensured that the examination subject is positioned such that that region of the body that has been prepared for the medical imaging examination by means of the accessory unit is positioned in the isocenter. A region of the examination subject's body that is covered by the at least one accessory unit, for example by the local coil for the magnetic resonance examination, specifies the region of the body that has been prepared for the medical imaging examination. The user can be clearly alerted by the haptically presented feedback if the examination subject has been unfavorably positioned. Accordingly, the user can initiate a change in the position of the examination subject in relation to the isocenter and/or a change in the physical position of the at least one accessory unit.

In another embodiment, the at least one imaging parameter is an extent of a field of view. The field of view (FOV), also known as the examination region or acquisition volume, represents a volume that is imaged in the acquired medical image data. The at least one imaging parameter can be an extent of the field of view in an axial direction, along a longitudinal axis and/or head-to-foot direction of the examination subject. The extent of the field of view can in this case be dimensions and/or a size and/or a positioning of the field of view. The field of view for the medical imaging examination can be specified. At the same time the field of view for a localization measurement and/or an overview measurement (localizer, scout) can also advantageously be specified. By the inventive approach it is thus possible to obtain an immediate feedback on the choice of the field of view for the medical imaging examination. The feedback can be provided in relation to a size and/or a positioning of the field of view.

In another embodiment, the valid parameter range for the extent of the field of view includes a maximum size of the field of view that can be acquired in an imaging scan. The maximum size of the field of view is specified, for example, by the type of medical imaging, such as by the magnetic resonance sequence used in the case of a magnetic resonance examination. The maximum size of the field of view can in this case be stored in system specification parameters. In this way the feedback can be provided when the user has chosen a size for the field of view that is greater than the maximum size of the field of view. If this unduly large choice of the field of view is invalid and leads to non-functioning of the medical imaging, a continuous feedback, as described above, can be provided. If this unduly large choice of the field of view leads merely to a change in an imaging mode, for example to a setting of a multi-stage measurement, then the feedback can be provided only once, as also described above, simply as an alert to the change in the imaging mode.

In another embodiment, the planning environment is a graphical visualization of the examination subject, the at least one imaging parameter being specified on the graphical visualization of the examination subject. The graphical visualization of the examination subject can be, for example, a depiction of the examination subject on the touch display. Preferably the graphical visualization of the examination subject is an image of the examination subject in its position supported on the patient support apparatus. The depiction can be a realistic rendering of the examination subject in the form of a camera image and/or an abstract representation of the examination subject, such as of contours of the examination subject. The at least one imaging parameter can be particularly easily specified manually on the graphical visualization of the examination subject. An advantageous interaction of the user with the graphical visualization of the examination subject can take place in order to specify the at least one imaging parameter. For example, the user can indicate the position of the examination subject in relation to the isocenter directly on the graphical visualization. Thus, the user can select directly on the graphical visualization which region of the examination subject's body is to be positioned in the isocenter. A field of view for the medical imaging can also be specified particularly easily on the graphical visualization, for example by zooming using a two-fingered pinching gesture.

In another embodiment, the graphical visualization of the examination subject is generated on the basis of an evaluation of positional data of the examination subject, the positional data being acquired before the examination subject is introduced into a patient receiving zone of the medical imaging device. Positional data of the examination subject means positional data of the examination subject in relation to a patient support apparatus on which the examination subject is supported and positioned for the upcoming medical imaging examination. The positional data can also include a mapping and/or information concerning a position of the at least one accessory unit for the medical imaging examination. The positional data of the examination subject is advantageously acquired by a positional data acquisition unit. The positional data acquisition unit can be a camera, for example, that for acquires two-dimensional or three-dimensional positional data. In this way current positional data of the examination subject can particularly advantageously be available for the specification of the at least one imaging parameter, such that a current position of the examination subject can always be taken into account for the specification of the at least one imaging parameter. The positional data acquisition unit can be embodied independently of or separately from a detector unit of the medical imaging device. For example, the positional data acquisition unit can be a camera and the detector unit a scanner for acquiring magnetic resonance data. Particularly advantageously, the positional data maps the examination subject, at least approximately, in full, as a result of which a particularly simple acquisition of the positional data of the examination subject can be achieved, since for this purpose the examination subject must simply be brought into an acquisition range of the positional data acquisition unit. A full mapping of the patient means that the positional data maps and/or represents the examination subject, in particular a surface and/or a contour of the examination subject, in the direction of its longitudinal extension in its entirety and/or completely. Preferably the examination subject is mapped in a view of the examination subject from above. In this way the graphical visualization of the examination subject can be advantageously generated for the purpose of planning the medical imaging examination.

In another embodiment, the information is provided in the form of a vibration. In this case, components and/or a frame of the touch display vibrate. In this way the user can receive a clear alert and/or a clear feedback in response to the specified at least one imaging parameter. The vibration can in this case be continuous or occur once only, as described above. The vibration of the touch display is effected by motors integrated in the touch display that exhibit an unbalance.

In another embodiment, the information is provided in the form of a change in shape of a surface of the touch display, the touch display comprising at least one physical element which causes the change in shape of the surface of the touch display if there is a change in position. For this purpose the touch display can be embodied in multiple layers. Furthermore, the touch display can change its shape automatically and/or actively. Accordingly, the touch display can comprise at least one physical element, for example at least one physical button and/or control element and/or alert element. The at least one physical element can be projected out of the flat touch display and/or stand proud of the touch display in a tactile manner. Subsequently, the at least one physical element can also be retracted back into the touch display again without trace, such that the touch display is flat once more. In this way a particularly advantageous adaptive interface can be provided by means of the touch display. Accordingly, the touch display can change itself actively for the purpose of providing the information.

In another embodiment, the information is provided in the form of a tactile texture on the touch display. In this case a surface of the touch display can be changed in such a way that tactile structures are produced on the surface. This is accomplished preferably by means of electrostatic forces. The electrostatic forces can act in particular between the finger of a user and the touch display. In this way a sense of physical structures, for example of contours and/or edges and/or a surface finish, can be conveyed to the user even though the touch display itself is smooth. The tactile texture can be the tactile structures and/or contours and/or edges and/or the tactile surface finish of the touch display. By means of this approach the user can be provided with valuable supplementary information and/or meaningful feedback relating to the specified at least one imaging parameter.

In another embodiment, a contour of the body of the examination subject is determined on the basis of the positional data of the examination subject, the contour of the examination subject's body being provided in the form of the tactile texture on the touch display. A mapping of the contour of the body of the examination subject is provided in the form of the tactile texture on the touch display. The examination subject can for example be provided with a texture which stands out from an environmental region of the examination subject. Alternatively or in addition, the contours of the examination subject and/or the entire examination subject can be embodied as elevated, in particular in a haptically sensible manner on the touch display, with respect to the environmental region of the examination subject. The information relating to the contour of the body of the examination subject can allow a simple specification of the at least one imaging parameter, in particular with regard to a position and/or an anatomy of the examination subject. In this way a more accurate positioning of the field of view and/or of a position of the examination subject in relation to an isocenter can be made possible, for example. The tactile texture can convey the contours of the examination subject to the user particularly clearly. In particular it is also possible in this way to specify the at least one imaging parameter without having to look at the touch display.

In another embodiment, a position of at least one accessory unit for the medical imaging examination is detected, the detected position of the at least one accessory unit being provided in the form of the tactile texture on the touch display. The detection of the position of the at least one accessory unit can be accomplished by means of the acquisition of positional data of the examination subject as described in greater detail above. The position of the at least one accessory unit can accordingly be taken into account particularly easily in the planning of the medical imaging session.

The inventive graphical interface unit for a medical imaging device has a touch display, a provider unit, a specification unit and an information unit, the graphical interface unit being embodied for carrying out the inventive method.

The inventive graphical interface unit is accordingly embodied for carrying out a method for planning a medical imaging examination of an examination subject by means of a medical imaging device. The provider unit is configured to provide a planning environment for the planning of the medical imaging examination on a touch display of the graphical interface unit. The specification unit is configured to specify at least one imaging parameter for the medical imaging examination by a manual input on the touch display. The information unit is configured to provide information on the touch display, the information being presented haptically on the touch display.

The inventive medical imaging apparatus has such an inventive graphical interface unit. The graphical interface unit can be embodied for the purpose of sending control signals to the medical imaging device and/or receiving and/or processing control signals in order to carry out an inventive method. The graphical interface unit can be integrated in the medical imaging device. The graphical interface unit can also be installed separately from the medical imaging device. The graphical interface unit can be connected to the medical imaging device.

A non-transitory, computer-readable data storage medium in accordance with the invention can be loaded directly into a memory of a programmable processor of a graphical interface unit and has program for carrying out the inventive method when the program code is executed in the processor of the graphical interface unit. As a result the inventive method can be implemented quickly, in identically repeatable fashion and robustly. The processor must satisfy certain preconditions, such as having an appropriate random access memory, an appropriate graphics card or an appropriate logic unit for example, so that the respective method steps can be executed efficiently. Examples of electronically readable data media are a DVD, a magnetic tape or a USB stick on which electronically readable control information, in particular software (cf. above), is stored.

The advantages of the inventive graphical interface unit, the inventive medical imaging apparatus and the inventive storage medium substantially correspond to the advantages of the inventive method, which have been explained in detail. Features, advantages or alternative embodiment variants mentioned in this context also apply to the other aspects of the invention. The functional features of the method are in this case embodied by corresponding device-related modules, in particular by hardware modules.

DESCRIPTION OF THE PREFERRED EMBODIMENTS

Figure 1:
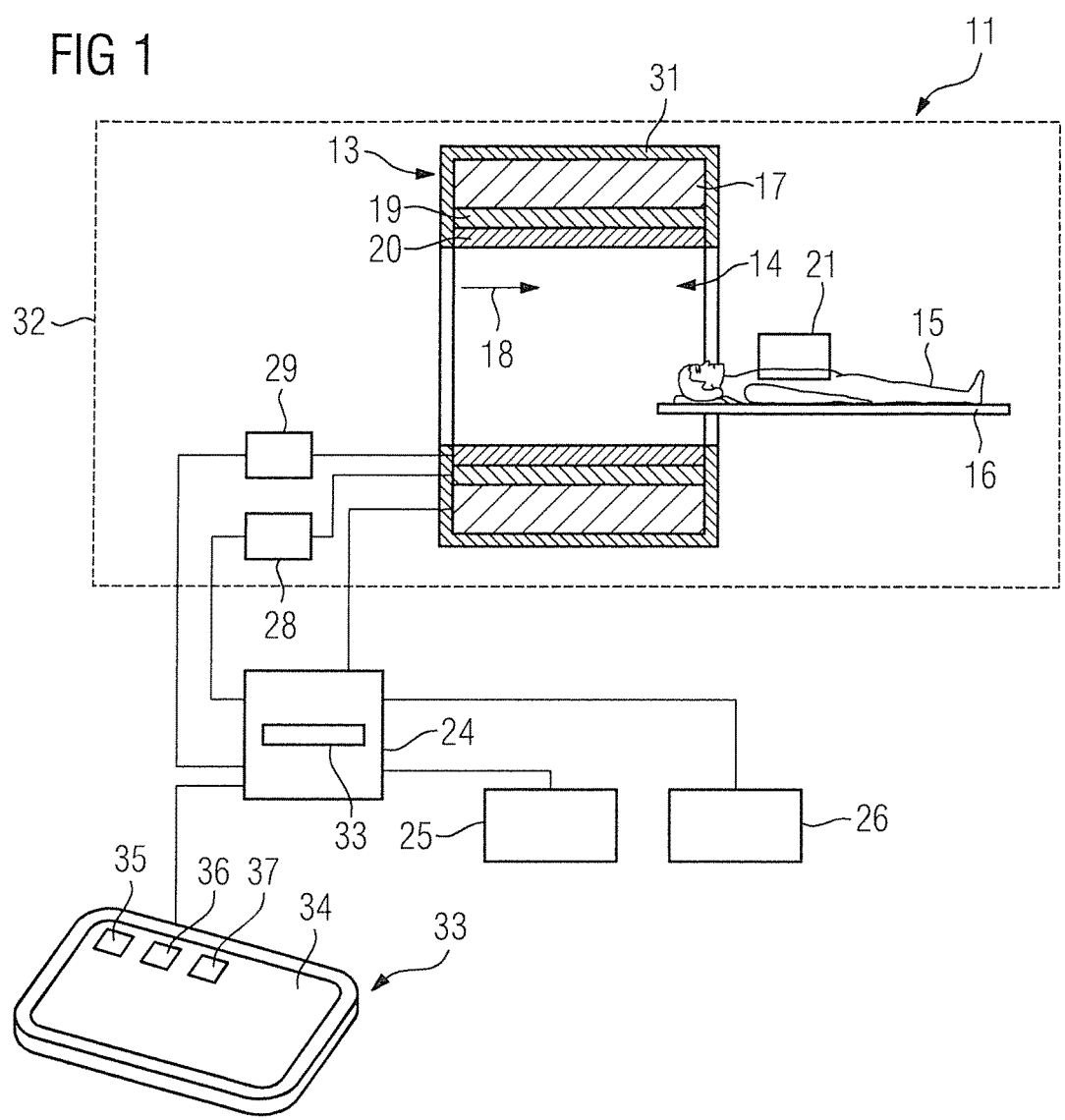
FIG. 1 shows an inventive medical imaging apparatus with an inventive graphical interface unit in a schematic representation.

FIG. 1 shows an inventive medical imaging apparatus with an inventive graphical interface 33 in a schematic presentation.

The medical imaging apparatus can be, for example, a magnetic resonance apparatus, a single-photon emission tomography apparatus (SPECT apparatus), a positron emission tomography apparatus (PET apparatus), a computed tomography apparatus, an ultrasound apparatus, an X-ray apparatus or a C-arm apparatus. In this regard, a combined medical imaging apparatus composed of an arbitrary combination of a number of the cited imaging modalities is also possible. In the case shown, the medical imaging apparatus is embodied by way of example as a magnetic resonance apparatus 11.

The magnetic resonance apparatus 11 has a detector unit formed by a magnet unit 13 and having a basic field magnet 17 for generating a strong and constant basic magnetic field 18. In addition, the magnetic resonance apparatus 11 has a cylinder-shaped patient receiving zone 14 for accommodating an examination subject 15, in the present case a patient. The patient receiving zone 14 is cylindrically enclosed by the magnet unit 13 in a circumferential direction. The patient 15 can be introduced into the patient receiving zone 14 by a patient support 16 of the magnetic resonance apparatus 11. For this purpose, the patient support 16 has a patient transport table that is movable within the magnetic resonance magnet unit 13. The magnet unit 13 is shielded externally by a housing enclosure 31.

The magnet unit 13 additionally has a gradient coil arrangement 19 for generating magnetic field gradients that are used for spatial encoding during imaging. The gradient coil arrangement 19 is driven by a gradient control processor 28. The magnet unit 13 furthermore has a radio-frequency antenna arrangement 20 that, in the case shown, is embodied as a whole body coil permanently integrated in the magnet unit 13, and a radio-frequency antenna control processor 29 for exciting nuclear spins in the subject 15 so as to deviate from the polarization established by the basic magnetic field 18 generated by the basic field magnet 17. The radio-frequency antenna arrangement 20 is driven by the radio-frequency antenna control processor 29 and radiates radio-frequency magnetic resonance sequences into an examination chamber that is substantially formed by the patient receiving zone 14. The radio-frequency antenna arrangement 20 may be embodied for receiving magnetic resonance signals from the patient 15.

The shown magnetic resonance apparatus 11 has a radio-frequency coil 21 configured for receiving magnetic resonance signals. In this case the radio-frequency coil 21 forms an accessory unit for the magnetic resonance imaging. For the purposes of a magnetic resonance examination, the radio-frequency coil 21 is applied by a medical operator to a region of the body of the examination subject 15 that is to be examined. In the resent exemplary embodiment, the radio-frequency coil 21 is formed by an antenna unit that encompasses a body portion. The radio-frequency coil 21 may alternatively be a knee antenna and/or back antenna of any other type of local coil. It is also conceivable for more than one radio-frequency coil 21 to be positioned on the examination subject 15. Typically, up to ten radio-frequency coils 21 are used for acquiring the magnetic resonance signals.

The magnetic resonance apparatus 11 has a computer 24 for controlling the basic field magnet 17, the gradient control processor 28 and the radio-frequency antenna control processor 29. The computer 24 is responsible for the centralized control of the magnetic resonance apparatus 11, such as performing a predetermined imaging gradient echo sequence. Control information such as imaging parameters, as well as reconstructed magnetic resonance images can be provided for a user on an output interface 25, in the present case a display monitor, of the magnetic resonance apparatus 11. The magnetic resonance apparatus 11 additionally has an input interface 26 via which information and/or parameters can be entered by a user during a measurement procedure. The computer 24 can include the gradient control processor 28 and/or the radio-frequency antenna control processor 29 and/or the output interface 25 and/or the input interface 26. The components within the outline 32 are commonly called a magnetic resonance data acquisition scanner.

The illustrated magnetic resonance apparatus 11 can of course have further components that are ordinarily present in magnetic resonance apparatuses. The general principles of operation of a magnetic resonance apparatus are furthermore known to those skilled in the art, so a detailed description of the further components is not necessary herein.

In the case shown, the graphical interface 33 has a touch display 34, thus enabling information and/or data to be entered and presented directly via the graphical interface 33. In addition, the graphical interface unit has a provider unit 35, a specification unit 36 and an information unit 37. Typically, the graphical interface 33 also has a control unit (not shown) which can include a computing module. All of these modules or units are processors or portions of a processor. The magnetic resonance apparatus 11 is accordingly configured in combination with the graphical interface 33 for performing an inventive method for planning a medical imaging examination of the examination subject 15. To that end the graphical interface 33 advantageously engages in a data exchange with the magnetic resonance apparatus 11, in particular the computer 24 of the magnetic resonance apparatus 11. In this way an examination of the examination subject 15 can be performed by the magnetic resonance apparatus 11 on the basis of the at least one imaging parameter specified on the graphical interface 33. Alternatively to the visualization, the graphical interface 33 can be configured on its own for implementing the inventive method for planning a medical imaging examination of the examination subject 15.

The graphical interface 33 is arranged inside the examination room. For example, the graphical interface 33 can be arranged directly on the housing enclosure 31 of the magnet unit 13. In this case the graphical interface 33 can be arranged directly on a front panel of the housing enclosure 31. The arrangement of the graphical interface 33 on the housing enclosure 31, in particular on the front panel of the housing enclosure 31, can be done by an integration of the graphical interface 33 into the housing enclosure 31. In this case the front panel of the housing enclosure 31, in particular a front housing shell of the housing enclosure 31, can have a recess for integration of the graphical interface 33. Alternatively, the graphical interface 33 can be arranged on the patient support 16 of the magnetic resonance apparatus 11. It is also conceivable for the graphical interface 33 to be embodied mechanically independently of the magnetic resonance apparatus 11. The graphical interface 33 can accordingly be moved independently of the magnetic resonance apparatus 11 in the examination room. It is also conceivable for a planning of the examination by the magnetic resonance apparatus 11 to take place with the graphical interface 33 from outside the examination room.

Figure 2:
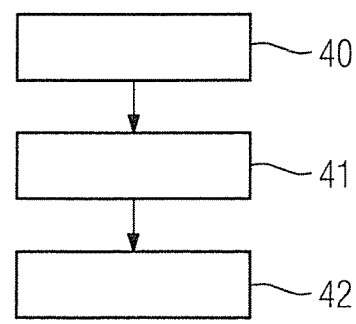
FIG. 2 is a flowchart of a first embodiment of the inventive method.

FIG. 2 is a flowchart of a first embodiment variant of an inventive method for planning a medical imaging examination of an examination subject 15 by operation of a medical imaging apparatus.

In a first method step 40, a planning environment for the planning of the medical imaging examination is provided by means of the provider unit 35 on the touch display 34 of the graphical interface 33.

In a further method step 41, at least one imaging parameter is specified for the medical imaging examination by the specification 36 and by a manual input on the touch display 34.

In a further method step 42, information is provided on the touch display by the information unit 37, the information being presented haptically on the touch display 34.

Figure 3:
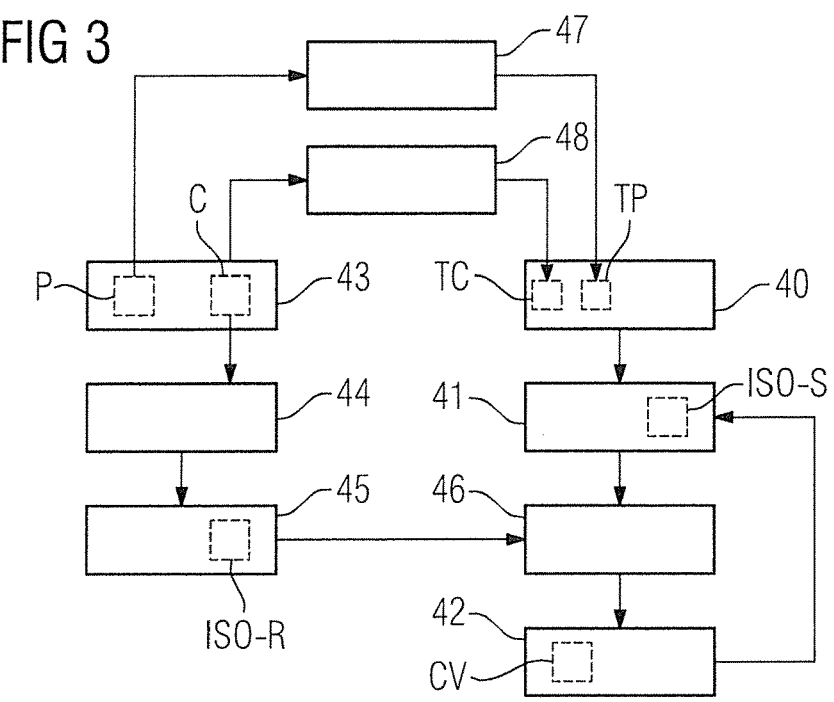
FIG. 3 is a flowchart of a second embodiment of the inventive method.

FIG. 3 shows a flowchart of a second embodiment of an inventive method for planning a medical imaging examination of an examination subject 15 by a medical imaging apparatus.

The following description is limited itself essentially to the differences compared to the exemplary embodiment in FIG. 2, reference being made to the description of the exemplary embodiment in FIG. 2 with respect to method steps that remain the same. Method steps that remain substantially the same are labeled consistently with the same reference numerals.

The embodiment of the inventive method shown in FIG. 3 essentially includes the method steps 40, 41, 42 of the first embodiment variant of the inventive method according to FIG. 2. In addition, the embodiment variant of the inventive method shown in FIG. 3 has additional method steps and sub-steps. An alternative method execution sequence to FIG. 3 which includes only some of the additional method steps and/or sub-steps represented in FIG. 2 is also conceivable. Obviously, an alternative method execution sequence to FIG. 3 can also include additional method steps and/or sub-steps.

The exemplary embodiment shown in FIG. 3 illustrates the possibility of making use of the planning environment to set a position of the examination subject 15 in relation to an isocenter of the medical imaging apparatus 11. A haptically presented feedback in response thereto can then be advantageously provided directly on the touch display. The approach is illustrated again in FIG. 4. This application of the inventive method is to be regarded as exemplary only. At least some of the method steps shown can also be used for other applications.

In a further method step 43, positional data of the examination subject 15 is acquired before the examination subject 15 is introduced into the patient receiving zone 14 of the medical imaging device. The further method step 43 accordingly takes place prior to the planning of the medical imaging examination in the further method step 40. The acquisition of the positional data is accomplished in particular by a positional data acquisition unit, for example by means of a camera mounted on the medical imaging device. In this case acquiring the positional data in the further method step 43 includes an acquisition of examination subject positional data P of the examination subject 15. In addition, the acquisition of the positional data includes an acquisition of accessory unit positional data C of at least one accessory unit for the medical imaging examination.

On the basis of the accessory unit positional data C, an accessory unit position of the at least one accessory unit can be detected in a further method step 48. Providing a planning environment in the further method step 40 can then include providing the detected position of the at least one accessory unit in the form of a tactile accessory unit texture TC on the touch display 33. An advantageous provision of information on the touch display accordingly takes place already in method step 40, the information being presented haptically on the touch display as a tactile texture.

In a further method step 47, a contour of the body of the examination subject 15 can be determined on the basis of the examination subject positional data P of the examination subject 15. The contour of the body of the examination subject 15 can then be provided in the further method step 40 in the form of a tactile examination subject texture TP on the touch display 33. An advantageous provision of information on the touch display accordingly takes place already in method step 40, the information being presented haptically on the touch display as a tactile texture. As described with reference to FIG. 5, a graphical visualization of the examination subject 15 can also be generated on the basis of the examination subject positional data P and be provided on the touch display 33 in the further method step 40.

Figure 4:
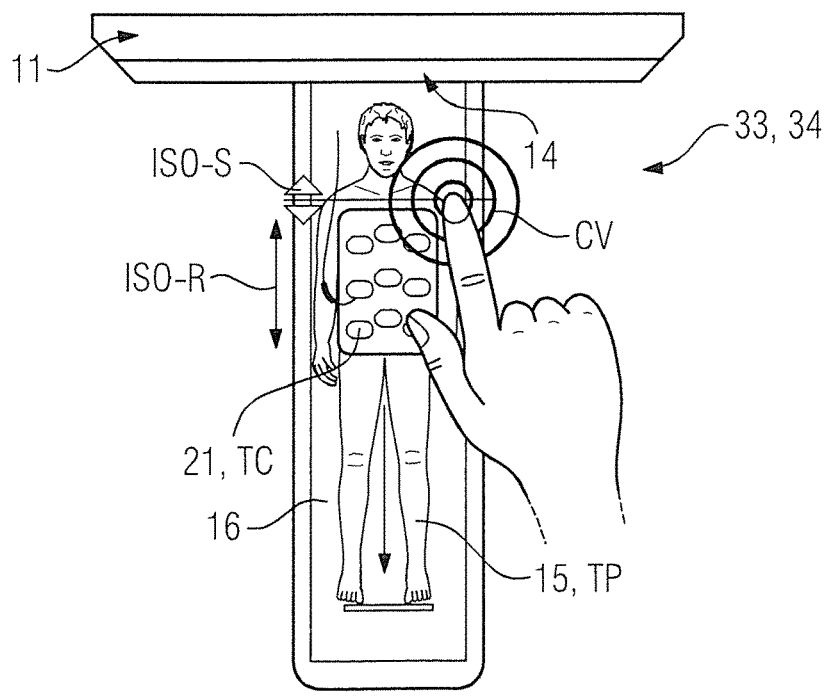
FIG. 4 shows an example of the inventive approach according to the second embodiment of the inventive method.

Such a graphical visualization of the examination subject 15, the latter being positioned on the patient support apparatus 16, is shown in FIG. 4. The examination subject 15 is prepared in particular for a magnetic resonance examination. The inventive approach is of course also conceivable for other medical imaging examinations using other imaging modalities. The examination subject 15 is still positioned outside of the patient receiving zone 14 of the magnetic resonance apparatus 11. An accessory unit, more specifically a local radio-frequency antenna unit 21, is positioned on the examination subject 15.

In this case FIG. 4 shows in particular a section of the touch display 33, in particular the provider device 34 of the planning environment. Shown is a view from above onto the examination subject 15, on which the planning of the medical imaging examination can be carried out.

It is also shown in FIG. 4 that the tactile examination subject texture TP is provided on the touch display 33. Accordingly, the user can tangibly sense the contours of the examination subject 15 and/or the examination subject 15 itself particularly easily on the touch display 33 his or her finger. The tactile accessory unit texture TC is likewise shown on the touch display 33. The user can accordingly tangibly sense the position of the local radio-frequency antenna unit 21 particularly advantageously on the touch display 33.

In the further method step 41, an isocenter position ISO-S of the examination subject 15 in relation to an isocenter of the medical imaging device is now specified, by a manual input on the part of the user.

On the basis of the accessory unit positional data C acquired in the further method step 43, a position of the at least one accessory unit for the medical imaging examination can be detected in a further method step 44. In a further method step 45, a region of the body of the examination subject 15 that has been prepared for the medical imaging examination can accordingly be determined on the basis of the detected position of the at least one accessory unit. Said region of the body that has been prepared for the medical imaging examination can represent a valid isocenter parameter range ISO-R for the position of the examination subject 15 in relation to the isocenter.

In a further method step 46, the at least one specified imaging parameter is compared with a parameter range for the at least one imaging parameter. In the case shown, a comparison of the input isocenter position ISO-S with the determined isocenter parameter range ISO-R is carried out in method step 46. A check is made as to whether the at least one specified imaging parameter lies outside of the valid parameter range for the at least one imaging parameter. In this way it is checked whether the user has specified an isocenter position ISO-S of the region of the body of the examination subject 15 that lies outside of the isocenter parameter range ISO-R.

If the result of the comparison of the at least one specified imaging parameter with the parameter range is that the at least one specified imaging parameter lies outside of the valid parameter range for the at least one imaging parameter, then the feedback is provided haptically on the touch display 33 in the further method step 42. The feedback is accordingly provided haptically on the touch display 33 as a function of a result of the comparison. In the present case the feedback is provided when the user has specified the isocenter position ISO-S outside of the isocenter parameter range ISO-R.

The feedback in response to the specification of the at least one imaging parameter in the further method step 42 on the touch display 33 can be provided in the form of a vibration CV. In this case the vibration CV can be generated continuously until a specification of the at least one imaging parameter falls within the valid parameter range, i.e. until the user specifies the isocenter position ISO-S within the isocenter parameter range ISO-R.

Alternatively or in addition, if the touch display 33 is embodied in multiple layers, the feedback can also be provided in the form of an active change in shape of the multilayer touch display 33. Alternatively, the feedback can also be provided in the form of a tactile texture on the touch display 33.

FIG. 4 can further explain this approach with an example. It can be seen that the isocenter parameter range ISO-R extends over a longitudinal side of the local radio-frequency antenna unit 21. This is because that region of the body of the examination subject 15 which is covered by the local radio-frequency antenna unit 21 has been prepared for the magnetic resonance examination.

The isocenter position ISO-S should accordingly also be specified within the isocenter parameter range ISO-R. In this case the isocenter position forms in particular that point along the longitudinal direction of the examination subject 15 which is to be positioned in the isocenter of the magnetic resonance apparatus 11 for the purposes of the medical imaging examination. It is beneficial that the isocenter position ISO-S is to be positioned within the isocenter parameter range ISO-R so that an optimal acquisition of the magnetic resonance signals by means of the radio-frequency antenna unit 21 can take place during the magnetic resonance examination.

In the present case, however, the user has chosen an isocenter position ISO-S outside of the isocenter parameter range ISO-R by means of the manual input. In the present case the user has simply tapped on his or her desired isocenter position ISO-S in the longitudinal direction of the examination subject 15. The user can thereupon be made aware of his or her unfavorable choice of the isocenter position ISO-S directly on the touch display 33 by means of the continuous vibration CV. The vibration can continue for as long as it takes for the isocenter position ISO-S to be changed by the user in such a way that it lies within the isocenter parameter range ISO-R.

Figure 5:
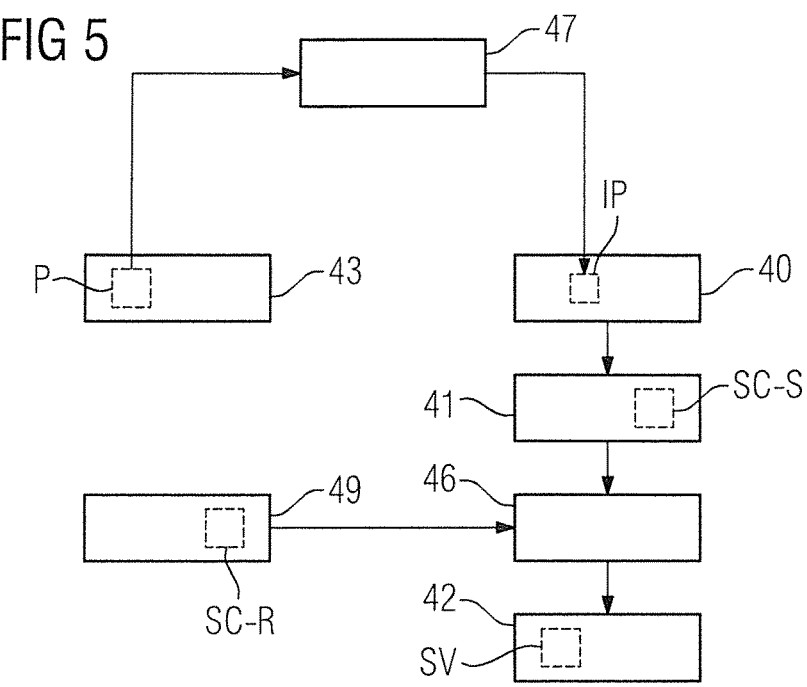
FIG. 5 is a flowchart of a third embodiment of the inventive method.

FIG. 5 shows a flowchart of a third embodiment of an inventive method for planning a medical imaging examination of an examination subject 15 by means of a medical imaging device.

The following description is limited itself essentially to the differences compared to the exemplary embodiment in FIG. 2, reference being made to the description of the exemplary embodiment in FIG. 2 with respect to method steps that remain the same. Method steps that remain substantially the same are labeled consistently with the same reference numerals.

The embodiment variant of the inventive method shown in FIG. 5 essentially includes the method steps 40, 41, 42 of the first embodiment of the inventive method according to FIG. 2. In addition, the embodiment of the inventive method shown in FIG. 5 includes additional method steps and sub-steps. An alternative method execution sequence to FIG. 5 which includes only some of the additional method steps and/or sub-steps represented in FIG. 2 is also conceivable. Obviously, an alternative method execution sequence to FIG. 5 can also include additional method steps and/or sub-steps.

The exemplary embodiment shown in FIG. 5 illustrates the possibility of making use of the planning environment to set an extent of a field of view for the medical imaging examination. A feedback in response thereto can then be advantageously provided directly on the touch display 33. The approach is illustrated again in FIG. 6 for purpose of explanation. This application of the inventive method is to be regarded as exemplary only. At least some of the method steps shown can also be used for other applications.

In the further method step 43, examination subject positional data P of the examination subject 15 is acquired once again, as already described with reference to FIG. 3. A graphical visualization IP of the examination subject 15 is now generated in a further method step 47 on the basis of an evaluation of said examination subject positional data P. Said graphical visualization IP of the examination subject 15 can now be presented on the planning environment as an image on the touch display 33 in the further method step 40. The at least one imaging parameter can then be specified on the graphical visualization IP of the examination subject 15. The graphical visualization IP of the examination subject 15 is likewise shown in FIG. 4 and FIG. 6 as an image of the human patient that is positioned on the patient support apparatus 16. It is of course also possible once again to provide information relating to a contour of the body of the examination subject 15 and/or a contour of the at least one accessory unit also in accordance with the approach shown in FIG. 5.

In the further method step 41, an extent SC-S of the field of view for the medical imaging examination is specified as imaging parameter. In a further method step 49, a maximum size SC-R of the field of view which can be acquired in an imaging scan is provided. The maximum size SC-R of the field of view represents in particular the valid parameter range for the extent SC-S of the field of view.

If a comparison of the specified extent SC-S of the field of view with the maximum size SC-R of the field of view now yields as result in a further method step 46 that the specified extent SC-S is greater than the maximum size SC-R, then a haptically presented feedback SV can be provided as an alert for the user in the further method step 42. In this case the feedback is provided in particular once only, as soon as the field of view has been set such that its specified extent SC-S exceeds the maximum size SC-R. This is because a consequence thereof can be a switchover of an imaging mode, for example into a multi-station acquisition. The once-only feedback, which is embodied for example as a vibration, can be an alert to the switchover of the imaging mode. If the overlarge setting of the field of view constitutes an error situation, a continuous feedback is also beneficial. Alternatively or in addition, if the touch display 33 is embodied in multiple layers, the feedback can also be provided in the form of an active change in shape of the multilayer touch display 33. Alternatively, the feedback can also be provided in the form of a tactile texture on the touch display 33.

Figure 6:
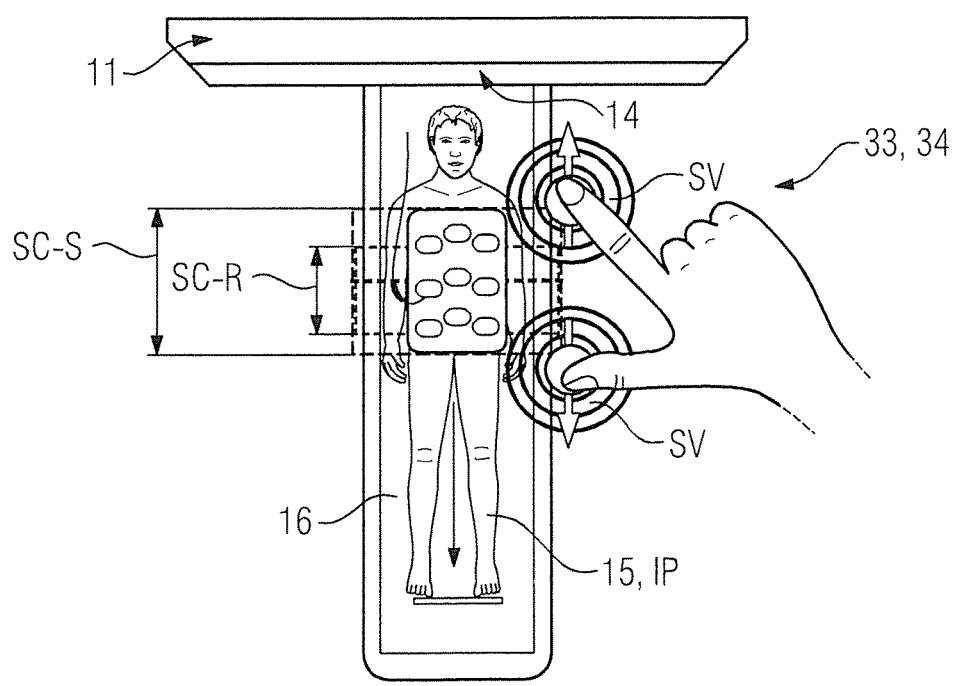
FIG. 6 shows an example of the inventive approach according to the third embodiment of the inventive method.

The approach according to FIG. 5 is illustrated again in FIG. 6. As in FIG. 5, a view from above onto the examination subject 15, the latter being positioned on the patient support apparatus 16 of the magnetic resonance apparatus 11 outside of the patient receiving zone 14, is shown once again. In the case shown, a graphical visualization IP of the examination subject 15 is shown on the provider device 34 and/or the touch display 33.

In the case shown in FIG. 6, the extent SC-S of the field of view is specified by means of a manual gesture on the part of the operator. In the case shown, the operator zooms out the field of view directly on the graphical visualization IP of the examination subject 15 by means of a two-fingered pinching motion on the touch display 33. In so doing, in particular the extent SC-S of the field of view in the axial direction, in particular a first and a second limit for the field of view in the axial direction, is specified. The field of view can be specified for an overview measurement, for example. In the case shown, the extent SC-S of the field of view has been chosen such that it is greater than the maximum size SC-R of the field of view. A once-only vibration SV of the touch display 33 is thereupon provided as feedback. A switchover of an imaging mode can be initiated so as to allow imaging to take place over the entire extent SC-S of the field of view.

The method steps of the inventive method illustrated in FIGS. 2-6 are performed by the computer 24. To that end, the computer has the requisite software and/or computer programs that are stored in a memory of the computer 24. The software and/or computer programs have program code configured to perform the inventive method when the computer program and/or the software is executed in the computer by one or more processors of the computer.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for planning a medical imaging examination of an examination subject by operation of a medical imaging apparatus, said method comprising:
   providing a representation of a planning environment for planning of the medical imaging examination on a touch display of a graphical interface;
   making a manual input on the touch display that specifies at least one imaging parameter for said medical imaging examination, the at least one imaging parameter specifying a position of the examination subject with respect to an isocenter of said medical imaging apparatus on the touch display; and
   haptically providing information on said touch display in response to said manual input.

2. The method as claimed in claim 1, comprising: providing said information on said touch display as feedback dependent on the specification of said at least one imaging parameter.

3. The method as claimed in claim 2, comprising:
   comparing, using a processor of said graphical interface, the specified image parameter with a parameter range associated with said at least one imaging parameter; and
   providing said feedback dependent on a result of said comparing.

4. The method as claimed in claim 3, wherein said parameter range represents a valid parameter range for said at least one imaging parameter, and wherein providing said feedback on said touch display dependent on the result of said comparing to indicates that said at least one specified image parameter is outside of said valid parameter range for said at least one imaging parameter.

5. The method as claimed in claim 4, comprising:
   providing said feedback continuously until a further specification, made via said touch display, of said at least one imaging parameter is within said valid parameter range.

6. The method as claimed in claim 4, comprising:
   providing said feedback only once, as soon as said at least one imaging parameter is determined, by said comparing, to be outside of said valid parameter range.

7. The method as claimed in claim 1, wherein said parameter range represents a valid parameter range for said at least one imaging parameter,
   wherein providing said feedback on said touch display dependent on the result of said comparing indicates that said at least one specified image parameter is outside of said valid parameter range for said at least one imaging parameter, and
   wherein said valid parameter range is for said isocenter and comprises a region of a body of the examination subject that has been prepared for said medical imaging examination.

8. The method as claimed in claim 7, comprising:
   detecting a position of at least one accessory item for said medical imaging examination; and
   preparing said region of the body of the examination subject for said medical imaging examination dependent on the detected position of said at least one accessory item.

9. The method as claimed in claim 1, comprising:
entering said at least one imaging parameter as an extent of a field of view of said medical imaging apparatus.

10. The method as claimed in claim 9, wherein said parameter range represents a valid parameter range for said at least one imaging parameter,
wherein providing said feedback on said touch display dependent on the result of said comparing indicates that said at least one specified image parameter is outside of said valid parameter range for said at least one imaging parameter, and
wherein said valid parameter range is for said extent of said field of view and comprises a maximum size of said field of view that can be acquired in an imaging scan executed by said medical imaging apparatus.

11. The method as claimed in claim 1, comprising:
presenting said planning environment as a graphical visualization of said examination subject with said at least one imaging parameter being specified within said graphical visualization.

12. The method as claimed in claim 11, comprising:
generating said graphical visualization in said graphical interface dependent on an evaluation of positional data of the examination subject acquired before said examination subject is introduced into a patient receiving zone of said medical imaging apparatus.

13. The method as claimed in claim 1, comprising:
providing said information haptically as a vibration.

14. The method as claimed in claim 1, comprising:
providing said information haptically as a change in a shape of a surface of said touch display, wherein said touch display comprises at least one physical element that causes said change in said shape of said surface of said touch display when there is a change in position of said physical element.

15. The method as claimed in claim 1, comprising:
providing said information haptically as a tactile texture on said touch display.

16. The method as claimed in claim 15, comprising:
generating said graphical visualization in said graphical interface dependent on an evaluation of positional data of the examination subject acquired before said examination subject is introduced into a patient receiving zone of said medical imaging apparatus and comprising determining a contour of the body of the examination subject from positional data of the examination subject; and
configuring said tactile texture on said touch display to represent said contour of the body of the examination subject.

17. The method as claimed in claim 16, comprising:
detecting a position of at least one accessory item for said medical imaging examination and also configuring said tactile texture on said touch display to represent the detected position of said at least one accessory item.

18. A graphical interface for a medical imaging apparatus comprising:
a touch display;
a processor in communication with said touch display;
said processor being configured to provide a representation of a planning environment for planning of the medical imaging examination on a touch display of a graphical interface;
said touch display being configured to detect a manual input on the touch display that specifies at least one imaging parameter for said medical imaging examination and to enter an electronic signal representing said at least one imaging parameter into said processor, the at least one imaging parameter specifying a position of the examination subject with respect to an isocenter of said medical imaging apparatus on the touch display; and
said processor being configured to haptically provide information on said touch display in response to said manual input.

19. A medical imaging apparatus comprising:
a medical imaging device configured to implement an examination of an examination subject in said medical imaging device;
a graphical interface for said medical imaging device comprising a processor and a touchscreen;
said processor being configured to provide a representation of a planning environment for planning of the medical imaging examination on a touch display of a graphical interface;
said touch display being configured to detect a manual input on the touch display that specifies at least one imaging parameter for said medical imaging examination and to enter an electronic signal representing said at least one imaging parameter into said processor, the at least one imaging parameter specifying a position of the examination subject with respect to an isocenter of said medical imaging apparatus on the touch display; and
said processor being configured to haptically provide information on said touch display in response to said manual input.

20. A non-transitory, computer-readable data storage medium encoded with
programming instructions, said storage medium being loaded into a processor of a graphical interface for a medical imaging apparatus, and said programming instructions causing said processor to:
provide a representation of a planning environment for planning of the medical imaging examination on a touch display of a graphical interface;
detect a manual input on the touch display that specifies at least one imaging parameter for said medical imaging examination, the at least one imaging parameter specifying a position of the examination subject with respect to an isocenter of said medical imaging apparatus on the touch display; and
haptically provide information on said touch display in response to said manual input.

\* \* \* \* \*